June 27, 1944. W. I. BOWERS Plant Pat. 630
APRICOT TREE
Filed Sept. 28, 1943
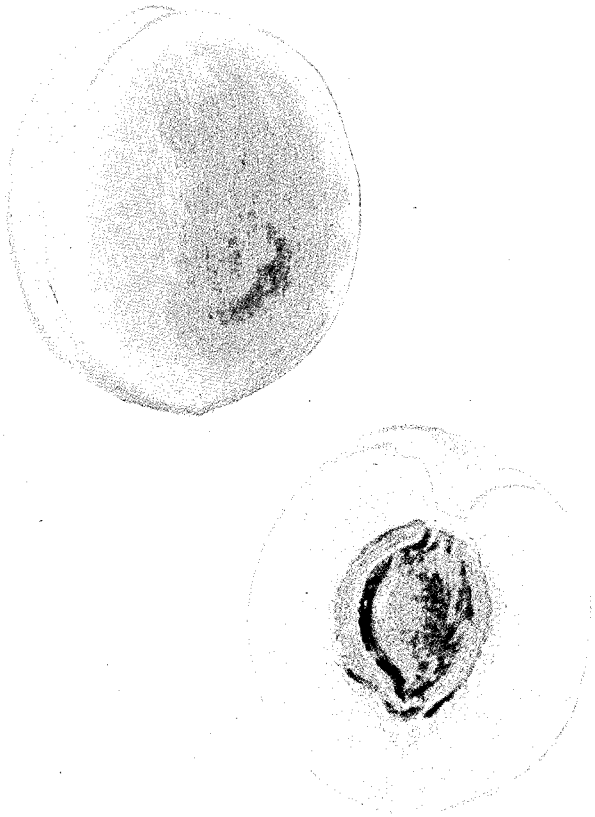
INVENTOR
William I. Bowers
By Orville M. Kile
PLANT PATENT AGENT Patented June 27, 1944

Plant Pat. 630

UNITED STATES PATENT OFFICE

630

APRICOT TREE

William I. Bowers, Yakima County, Wash.

Application September 28, 1943, Serial No. 504,158

1 Claim. (Cl. 47—62)

My present discovery relates to improvements in apricot varieties. Its novelty consists in an entirely new and desirable combination of desirable features of well-known apricot varieties.

This variety originated as a seedling found near a Yakimine tree in my orchards, and was possibly dropped by the Yakimine tree although there were other seeds planted there which might have come up and one of them produced this seedling. It will be necessary, therefore, to say that the parentage is unknown.

Although it is possible that the Yakimine apricot is the parent of this new variety and the shape of the trees of both varieties is similar, the fruit of the two varieties is vastly different. The fruit of my new variety has yellow flesh while the Yakimine has flesh of whitish color. My new apricot is slightly smaller than the Yakimine, ripens at a later season, and is a much better bearer and shipper.

The original illustration making a part of this specification shows a side view and a cross-section view of my new variety of apricot in approximately its true colors and slightly enlarged.

The variety has been asexually reproduced for a number of years and its characteristics have proved to be permanently fixed.

The tree is a vigorous grower and considerably like the Yakimine in shape. It is a regular and heavy producer of fruits.

The leaves are medium in size and similar to leaves of other apricot varieties.

A detailed description of the fruit is given below.

Fruit:

*Size.*—Average approximately 2⅛ inches in axial diameter and 2 inches in transverse diameter.

*Shape.*—Almost round, but slightly "blocky" or oval. Suture usually very shallow, cavity deep, apex without projecting point.

*Skin.*—Smooth; highly colored.

*Flesh.* — Fine-textured. Rich yellow to orange (approximately Capucine yellow, Plate III, Ridgway's Color Standards and Nomenclature).

*Flavor.*—Highly flavored, sweet and distinctive.

*Pit.*—Large, 1⅜ inches long by 1 inch wide. Winged; flat; free.

*Maturity.*—Very early, about with Riland.

The fruit of my new variety is more like that of the Riland (Plant Patent #74) than any other known variety, particularly in its color and ripening date. However, my variety has fruit that is larger and less "squat" in shape, has flesh of finer texture, slightly lighter color and higher flavor.

My variety is similar to the Wenatchee Moorpark in some respects, particularly in size, but much more highly colored and flavored, is rounder or less "squat" in shape, has smoother skin and an earlier ripening date.

This new variety is an excellent commercial variety since it comes early in the season when there are few varieties available, is a heavy bearer of good quality fruit which is appealing to the eye because of its good color, and presumably it would be a good commercial canner since it has been home-canned very successfully for several years.

Having thus disclosed my discovery, I claim:

The new and useful variety of apricot tree, substantially as herein shown and described, characterized by its vigorous growth and its prolific production of good-sized "blocky" or oval fruit with an early ripening season, smooth and highly colored skin, and flesh of sweet distinctive flavor, fine texture and deep yellow color.

WILLIAM I. BOWERS.